(12) United States Patent
Barbier et al.

(10) Patent No.: US 9,623,017 B2
(45) Date of Patent: Apr. 18, 2017

(54) 4:3 NALTREXONE: 5-METHYL-2-FURALDEHYDE COCRYSTAL

(71) Applicant: PAIN THERAPEUTICS, INC., Austin, TX (US)

(72) Inventors: Remi Barbier, Austin, TX (US); Nadav Friedman, Georgetown, TX (US); Vijay Srirambhatla, Birmingham (GB); Stephen Watt, East Lothian (GB); Michael Zamloot, Austin, TX (US)

(73) Assignee: PAIN THERAPEUTICS, INC., Austin, TX (US)

( * ) Notice: Subject to any disclaimer, the term of this patent is extended or adjusted under 35 U.S.C. 154(b) by 0 days.

(21) Appl. No.: 14/863,688

(22) Filed: Sep. 24, 2015

(65) Prior Publication Data

US 2016/0081946 A1  Mar. 24, 2016

Related U.S. Application Data

(60) Provisional application No. 62/054,515, filed on Sep. 24, 2014, provisional application No. 62/200,309, filed on Aug. 3, 2015.

(51) Int. Cl.
*A61K 31/485* (2006.01)
*A61K 31/341* (2006.01)
(Continued)

(52) U.S. Cl.
CPC ........ *A61K 31/4468* (2013.01); *A61K 9/7069* (2013.01); *A61K 31/00* (2013.01); *A61K 31/341* (2013.01); *A61K 31/485* (2013.01)

(58) Field of Classification Search
None
See application file for complete search history.

(56) References Cited

U.S. PATENT DOCUMENTS

| 4,559,222 A | 12/1985 | Enscore et al. |
| 8,338,444 B1 | 12/2012 | King et al. |

(Continued)

FOREIGN PATENT DOCUMENTS

| WO | 2004078163 A2 | 9/2004 |
| WO | 2016049266 A1 | 3/2016 |

OTHER PUBLICATIONS

International Search Report and Written Opinion in corresponding International Application No. PCT/US2015/051849, dated Dec. 17, 2015.

(Continued)

*Primary Examiner* — Nissa Westerberg
(74) *Attorney, Agent, or Firm* — J.A. Lindeman & Co., PLLC

(57) ABSTRACT

A 4:3 naltrexone: 5-methyl-2-furaldehyde cocrystal and its use as an opioid antagonist are disclosed. The invention also relates to a drug-in-adhesive transdermal patch containing the analgesic fentanyl, a mu opioid agonist, or an analog thereof and a 4:3 naltrexone: 5-methyl-2-furaldehyde cocrystal, as an opioid antagonist. A transdermal patch of the invention is tamper-resistant and an abuse deterrent which protects against drug misuse or abuse. The invention also provides a method of treating pain, such as acute, chronic, or intermittent pain, by applying a drug-in-adhesive transdermal patch according to the invention to the skin of a patient in need thereof. Also disclosed is an improved transdermal patch for administering fentanyl or an analog thereof, or for administering a mu opioid agonist, the improvement wherein the transdermal patch contains a 4:3 naltrexone: 5-methyl-2-furaldehyde cocrystal in an abuse limiting amount. The improved transdermal patch may be a drug-in-adhesive transdermal patch or a reservoir transdermal patch.

16 Claims, 17 Drawing Sheets

(51) Int. Cl.
    *A61K 9/70*           (2006.01)
    *A61K 31/4468*      (2006.01)
    *A61K 31/00*          (2006.01)

(56) References Cited

U.S. PATENT DOCUMENTS

| | | |
|---|---|---|
| 8,440,220 B2 | 5/2013 | Gale et al. |
| 8,747,889 B2 | 6/2014 | Gale et al. |
| 2004/0241218 A1 | 12/2004 | Tavares et al. |
| 2005/0095279 A1 | 5/2005 | Gale et al. |
| 2011/0182949 A1 | 7/2011 | Tang |
| 2013/0273119 A1 | 10/2013 | Engqvist et al. |

OTHER PUBLICATIONS

Duragesic US Prescribing Information, http://www.duragesic.com, accessed Aug. 11, 2014, pp. 1-39.
Guan et al., "I am in Pain!—A Case Report of Illicit Use of Transdermal Fentanyl Patches," Prim Care Companion CNS Disord. 2011, 13(5).
Schultheiss and Newman, "Pharmaceutical Cocrystals and Their Physiochemical Properties," Crystal Growth & Design, 2009, vol. 9, No. 6, pp. 2950-2967.

4:3 NALTREXONE: 5-METHYL-2-FURALDEHYDE COCRYSTAL

CROSS REFERENCE TO RELATED APPLICATIONS

This application claims priority to U.S. application Ser. No. 62/054,515 filed Sep. 24, 2104 and to U.S. application Ser. No. 62/200,309 filed Aug. 3, 2015, the disclosures of which are both incorporated herein by reference.

FIELD OF THE INVENTION

This invention relates to a 4:3 naltrexone: 5-methyl-2-furaldehyde cocrystal and its use as an opioid antagonist. The invention also relates to a transdermal patch, such as a drug-in-adhesive transdermal patch, containing an analgesic such as fentanyl, which is a mu opioid agonist, or an analog of fentanyl or another mu opioid agonist; and a 4:3 naltrexone: 5-methyl-2-furaldehyde cocrystal as an opioid antagonist. The invention also relates to methods for treating pain.

BACKGROUND OF THE INVENTION

Fentanyl is a synthetic opioid analgesic used to treat moderate to severe chronic pain. Fentanyl, whose chemical name is N-Phenyl-N-(1-(2-phenylethyl)-4-piperidinyl) propanamide, has the following chemical formula:

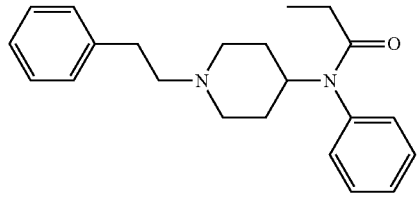 [SMILES: CCC(=O)N(c1ccccc1)C1CCN(CCc2ccccc2)CC1]

Fentanyl and its congeners, sufentanil, alfenanil, and remifentanil, all act as opioid agonists mainly on mu-receptors that are present along the central nervous system. Mu-binding sites are present in the human brain, spinal cord, and other tissues that are integral to the transmission of pain pathways. Therapeutic use of intravenous fentanyl results in a rapid onset but a short duration of action, making this route of administration a popular choice as an anesthetic adjuvant. Fentanyl's low molecular weight, high potency, and lipid solubility also makes it suitable for transdermal delivery. The development of transdermal fentanyl, a less invasive route of administration compared to intravenous delivery, has facilitated the use of fentanyl to manage chronic pain. Transdermal fentanyl patches, such as the DURAGESIC® fentanyl transdermal system sold by Janssen Pharmaceuticals, adhere to skin and provide a prolonged, continuous, slow, and therapeutic dose of fentanyl for up to 72 hours.

As with all potent mu opioid analgesics, fentanyl also is abused for its intense euphoric effects. Abusers seek rapid drug absorption. To get high, abusers often cut a small piece of the fentanyl patch and swallow it or suck on it. These actions provide abusers with a rapidly absorbed, high blood level of fentanyl, resulting in euphoric effects. Non-medicinal use of transdermal fentanyl patches is extremely dangerous and can result in opioid addiction, overdose, or death. Even after a 72 hour transdermal usage interval, some residual fentanyl remains in the patch. Unused or used fentanyl patches are therefore also susceptible to unintentional misuse, such as accidental exposure to a transdermal fentanyl patch by children or family pets.

Methods or paradigms of abusing fentanyl transdermal patches include, for example, single or multistep extraction, physical tampering with subsequent extraction and direct administration by oral routes such as chewing or swallowing, inhalation abuse (e.g., smoking) by heating or burning, or trans mucousal absorption across tissues in the oral cavity or across membranes in the rectal cavity. Documented methods of abusing fentanyl patches include injecting fentanyl extracted from a patch intravenously, chewing or swallowing patches, inserting patches into the rectum, inhaling fentanyl volatilized from the adhesive or gel, and extracting fentanyl in tea. The biological effects of fentanyl are similar to those of street heroin but fentanyl is approximately one hundred times more potent. It is extremely difficult to stop its absorption because fentanyl is highly lipophilic and penetrates the central nervous system easily. Therefore, the illicit use of fentanyl is very dangerous and causes numerous opioid overdose deaths. See, W. Guan, et al., Prim Care Companion CNS Disord. 2011, 13(5); http://www.ncbi.nlm.nih.gov/pmc/articles/PMC3267509/ (accessed Aug. 10, 2014).

Curtailing the misuse and abuse of fentanyl and other opioid analgesics is a difficult problem. Several approaches have been tried: formulation technologies aimed at introduction of functional characteristics that deter or resist physical and chemical practices that facilitate the non-medical use of the narcotics by various routes of administration. Such formulation technologies may impart one or more of the following abuse-deterrent characteristics to the narcotic drug product: tamper resistant secondary packaging, fabrication with crush or tear resistance laminate components, extraction resistance, formulation with prodrugs of the narcotic active ingredient, agonist and antagonist combinations, disposal systems that deactivate the residual fentanyl, and even nasal gels. For a discussion of these approaches, see U.S. Pat. No. 8,338,444 B1. While the prodrug approach modifies the drug itself, the other approaches look, at least to some extent, to formulation techniques.

Formulating or placing an opioid antagonist within the opioid agonist product is the basis of the agonist/antagonist approach to curtail misuse and abuse. If the opioid agonist product is misused or there is an attempt to extract the opioid agonist from the product, the opioid antagonist is released to decrease or even block the pharmacologic effect of the opioid agonist. U.S. Pat. Nos. 8,440,220 B2 and 8,747,889 B2 disclose an analgesic system for transdermal delivery of fentanyl and analogs thereof for analgesic purposes, to a subject through intact skin over an extended period of time. The disclosure of U.S. Pat. Nos. 8,440,220 B2 and 8,747,889 B2 are incorporated herein by reference. The transdermal analgesic system disclosed is reported to have reduced potential for abuse and a substantially minimized/negligible skin sensitization response from antagonist exposure. The transdermal analgesic system is intended to provide for the controlled release of the antagonist at a rate sufficient to provide an abuse limiting release rate ratio of the antagonist to the analgesic when the dosage form is subject to abuse. In this regard, the transdermal analgesic system is intended to provide release of the antagonist at a rate sufficient to block the opioid effects of the analgesic during abuse situations. The analgesic and antagonist layers are contained in distinct reservoir layers separated by an impermeable barrier layer. The transdermal analgesic system disclosed in U.S. Pat. Nos. 8,440,220 B2 and 8,747,889 B2, however, is not a preferred solution to potential abuse employing an antagonist reservoir and an antagonist release controlling means to modulate the ingress of water/solvent to the antagonist reservoir, to modulate the release of the antagonist during abuse while permitting the release of an antagonist at a rate to limit abuse. The transdermal analgesic system is thus complex in its formulation and in its manufacture.

In view of the existing and potential abuse and misuse of fentanyl transdermal patches there remains a need in the art to develop a fentanyl transdermal patch system which mitigates, neutralizes, or prevents the effects of fentanyl when a transdermal patch is intentionally abused or accidentally misused. This invention answers that need using a novel opioid analgesic/antagonist combination.

SUMMARY OF THE INVENTION

In one embodiment this invention relates to a 4:3 naltrexone: 5-methyl-2-furaldehyde cocrystal and its use as an opioid antagonist.

In another embodiment the invention also relates to a drug-in-adhesive transdermal patch containing the opioid analgesic fentanyl or an analog thereof and a 4:3 naltrexone: 5-methyl-2-furaldehyde cocrystal.

In another embodiment the invention also relates to a drug-in-adhesive transdermal patch containing a mu opioid agonist, such as fentanyl—disclosed here as a particular example, and a 4:3 naltrexone: 5-methyl-2-furaldehyde cocrystal, as an opioid antagonist.

Another embodiment of the invention relates to a method of treating pain, such as acute, chronic or intermittent pain, by applying a drug-in-adhesive transdermal patch according to the invention to the skin of a patient in need thereof.

DETAILED DESCRIPTION

Figure 1:
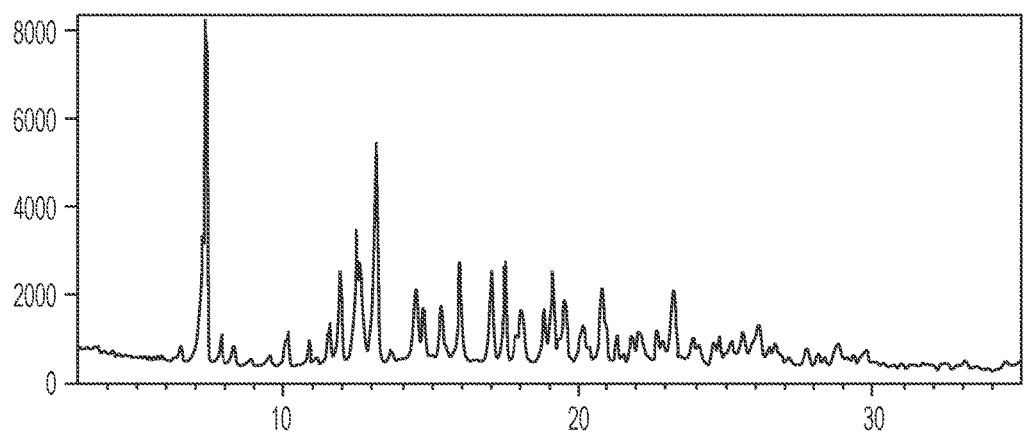
FIG. 1 depicts the experimental XRPD pattern of the 4:3 Naltrexone: 5-methyl-2-furaldehyde cocrystal prepared by grinding in Example 1.1.

Naltrexone, 17-(cyclopropylmethyl)-4,5α-epoxy-3,14-dihydroxymorphinan-6-one, is an opioid receptor antagonist, having the chemical structure shown below.

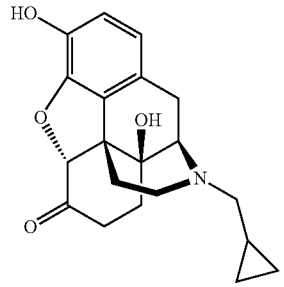

Pharmaceutical uses of naltrexone as an active pharmaceutical ingredient (API) include management of alcohol dependence, opioid overdose, and opioid dependence. U.S. Pat. Nos. 8,440,220 B2 and 8,747,889 B2 disclose naltrexone as an opioid antagonist used in their transdermal system.

In one embodiment, this invention relates to a 4:3 naltrexone: 5-methyl-2-furaldehyde cocrystal and its use as an opioid antagonist. It is well-known that crystalline materials obtain their fundamental physical properties from the molecular arrangement within the solid, and altering the placement and/or interactions between these molecules can, and usually does, have a direct impact on the properties of the particular solid. See, Schultheiss and Newman, "Pharmaceutical Cocrystals and Their Physiochemical Properties", *Crystal Growth & Design*, Vol. 9, No. 6, 2950-2967 (2009). Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates, permeability, hydrophilic or lipophilic character (important factors in determining drug delivery). Because these practical physical properties are influenced by the solid state properties of the crystalline form of the API, they can provide advantages for the pharmaceutical utility and formulation of the API.

Obtaining crystalline forms of an API is extremely useful in pharmaceutical development as it may affect the in vivo disposition of the active moiety, affect the rate or extent of its release from the dosage form, or even enable its suitability for a particular dosage form design. It also may permit better characterization of the API's chemical and physical properties. It is also possible to achieve desired properties of a particular API by forming a cocrystal of the API and a coformer. Crystalline forms often have better chemical and physical properties than the free base in its amorphous state. Another potentially important solid state property of an API is its dissolution rate in aqueous fluids or in polymeric preparations used to formulate the API. Such crystalline forms may, as with the cocrystal of the invention, possess more favorable pharmaceutical and formulation properties or be easier to process than known forms of the API itself.

This invention relates to a 4:3 naltrexone: 5-methyl-2-furaldehyde cocrystal, as described in the examples below. A cocrystal of an API, such as naltrexone, is a distinct chemical composition of the API and coformer(s) and generally possesses distinct crystallographic and spectroscopic properties when compared to those of naltrexone and 5-methyl-2-furaldehyde individually. Crystallographic and spectroscopic properties of crystalline forms are typically measured by X-ray powder diffraction (XRPD), single crystal X-ray crystallography, and infra-red spectroscopy, among other techniques. Cocrystals often also exhibit distinct thermal behavior. Thermal behavior is measured in the laboratory by such techniques as capillary melting point, thermogravimetric analysis (TGA), and differential scanning calorimetry (DSC). The 4:3 naltrexone: 5-methyl-2-furaldehyde cocrystal of the invention and the methods used to characterize it are described in the examples below.

In another embodiment, the invention relates to a drug-in-adhesive transdermal patch (also known as a monolithic transdermal patch) containing an analgesic such as fentanyl, which is a mu opioid agonist, or an analog of fentanyl or another mu opioid agonist; and a 4:3 naltrexone: 5-methyl-2-furaldehyde cocrystal as an opioid antagonist. This provides a tamper-resistant or abuse-deterrent transdermal fentanyl patch. The opioid agonist analgesic may be fentanyl or an analog thereof such as, but not limited to, alfentanil, lofentanil, remifentanil, sufentanil, and trefentanil. Fentanyl is a preferred opioid analgesic. Another embodiment of the invention relates to a drug-in-adhesive transdermal patch containing a mu opioid agonist and a 4:3 naltrexone: 5-methyl-2-furaldehyde cocrystal, as an opioid antagonist.

A drug-in-adhesive transdermal patch contains the drug to be delivered in an adhesive polymer matrix. The adhesive polymer matrix controls the release of the drug from a transdermal patch and its permeation through the skin. The adhesive polymer matrix contains the drug, and a pressure sensitive adhesive (PSA) comprised of one or more polymers suitable for adhesion to the skin. The adhesive polymer matrix and its method of preparation should be selected such that it is compatible with fentanyl or the fentanyl analog used and such that the crystalline form of the 4:3 naltrexone: 5-methyl-2-furaldehyde cocrystal is maintained. Examples of pressure sensitive adhesives include, but are not limited to, silicones/polysiloxanes, polyisobutylene (PIB), polyisoprene, polybutadiene, styrenic block copolymers, and the like. Examples of styrene block copolymer-based adhesives include, but are not limited to, styrene-isoprene-styrene block copolymer (SIS), styrene-butadiene-styrene copolymer (SBS), styrene-ethylene/butylene-styrene copolymers (SEBS), and di-block analogs thereof. These adhesive polymers are soluble in low polarity solvents and the matrix of the transdermal patch may be prepared by mixing the drug and cocrystal into the polymer solution followed by solvent casting of the matrix layer. Alternatively, a melt blending process in which the polymer is heated to achieve a sufficiently low viscosity to allow dry mixing of the drug and cocrystal may be employed. If the adhesive polymer matrix is formed by the melt blending and extrusion process, then polyacrylates and ethylene/vinyl acetate copolymers may be used in the adhesive polymer matrix in addition to the rubber-based adhesive polymers. Silicones are a preferred type of PSA polymers used in a drug-in-adhesive transdermal patch of the invention. Amine-compatible silicones PSA's, such as Dow Corning BioPSA 7-4101, are compatible with fentanyl free base and may be used in fentanyl-containing adhesive layers for that reason. Silicone PSAs have a low saturation solubility for fentanyl and its analogs. This allows for a zero order delivery rate of fentanyl while undissolved drug is present and after 72 hours less fentanyl remains in the patch, most having been delivered to the patient.

To prepare a drug-in-adhesive transdermal patch, the drug to be delivered, for example fentanyl or a fentanyl derivative, may first be dispersed in an oil and then the dispersion mixed into the adhesive polymer as is known the art. See, for example, U.S. Pat. No. 4,559,222, which is incorporated herein by reference. The 4:3 naltrexone: 5-methyl-2-furaldehyde cocrystal particles may also be dispersed in the oil as long as the cocrystal is not soluble or only sparingly soluble in the oil. Depending on the drug to be delivered and the adhesive polymer to be used, mineral oil or a silicone oil are common choices when considering PSA compatibility. The dispersion is mixed into the adhesive polymer using known blending techniques and at a shear rate that is not so high as to break up the adhesive polymer. As mentioned, silicone PSA's are a preferred type of adhesive for a drug-in-adhesive transdermal patch of the invention. An example of a silicone oil is Dow-Corning 360 Medical Fluid, a linear polydimethylsiloxane (PDMS) which is available in several different viscosities. Dow-Corning 360 Medical Fluid having a viscosity of 100 cSt is a preferred silicone oil.

Figure 9:
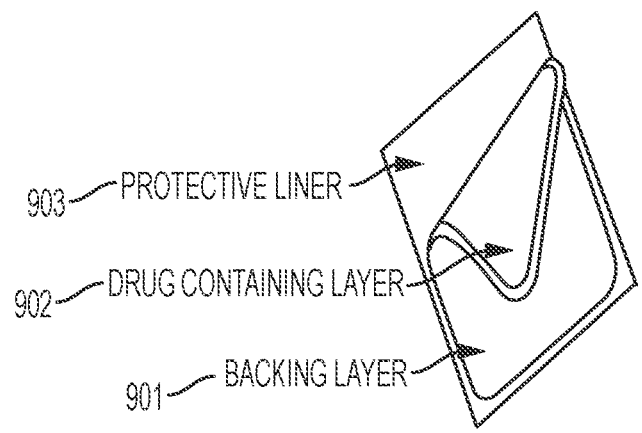
FIG. 9 depicts a drug-in-adhesive transdermal patch.

An example of a drug-in-adhesive transdermal patch used to deliver fentanyl is the DURAGESIC® fentanyl transdermal system sold by Janssen Pharmaceuticals. In the DURAGESIC® transdermal system, the amount of fentanyl released from each system per hour is proportional to the surface area (25 mcg/h per 10.5 $cm^2$). The composition per unit area of all system sizes is identical. The DURAGESIC® transdermal system, shown in FIG. 9, is a rectangular transparent unit comprising a protective liner and two functional layers. Proceeding from the outer surface toward the surface adhering to skin, these layers are: a backing layer 901 composed of polyester/ethyl vinyl acetate film; and a drug-in-adhesive layer 902. Before use, a protective liner (release sheet) 903 covering the adhesive layer is removed and discarded. See, DURAGESIC® US prescribing information, http://www.duragesic.com/sites/default/files/pdf/duragesic_0.pdf, (accessed Aug. 11, 2014). Other drug-in-adhesive transdermal patch structures and variations are known in the art.

In a drug-in-adhesive transdermal patch of the invention 4:3 naltrexone: 5-methyl-2-furaldehyde cocrystal particles are present in the drug-in-adhesive layer as a dispersion of particles along with the fentanyl or an analog thereof. In an embodiment of the invention, the drug-in-adhesive layer is a monolithic layer. As known in the art, fentanyl itself is partially or completely solubilzed in the adhesive polymer(s) making up the drug-in-adhesive layer and, thus, is present in the layer as a molecular dispersion with or without additional dispersed undissolved drug. The 4:3 naltrexone: 5-methyl-2-furaldehyde cocrystal is substantially or completely insoluble in the adhesive polymer(s), a solubility for the 4:3 naltrexone: 5-methyl-2-furaldehyde cocrystal of about 0 wt % to about 1 wt % of the total adhesive polymer composition. The relative solubility of the fentanyl and insolubility of the 4:3 naltrexone: 5-methyl-2-furaldehyde cocrystal provide a rate control mechanism allowing the fentanyl to be delivered to the skin and the cocrystal to be retained in the drug-in-adhesive layer. The 4:3 naltrexone: 5-methyl-2-furaldehyde cocrystal particles are typically distributed as a dispersed solid throughout the drug-in-adhesive layer to provide a uniform composition per unit area.

The 4:3 naltrexone: 5-methyl-2-furaldehyde cocrystal is soluble in water, aqueous media, certain organic solvents, and mixed aqueous-organic systems; however, its insolubility in the drug-in-adhesive layer does not permit its release in any substantial or therapeutic amount in response to the moisture which may be present at the skin surface during proper use of the transdermal patch. The drug-in-adhesive transdermal patch of the invention, however, does release naltrexone that dissociates from the 5-methyl-2-furaldehyde coformer present in the cocrystal at a rate and in an amount sufficient to provide an abuse limiting dose of the opioid antagonist to the opioid analgesic when subjected to non-medical use or accidental misuse. Thus, a drug-in-adhesive transdermal patch of the invention releases naltrexone which is the dissociation product of 4:3 naltrexone: 5-methyl-2-furaldehyde cocrystal as a result of the exposure to elevated temperature (i.e., a smoking paradigm of abuse) or an aqueous environment (e.g., water or other aqueous extraction solution or saliva depending on the paradigm of abuse), and provides sufficient naltrexone to decrease or block the pharmacologic effects of the opioid during abuse or misuse situations. A transdermal patch of the invention is therapeutically equivalent to a fentanyl-only patch when the patch is administered according to prescriptive practice for a legitimate medical purpose. When the patch experiences physical or chemical influences due to misuse, abuse, or is administered inconsistently with prescribed administration practice, e.g., swallowed, extracted, chewed, sucked on, smoked, etc., a transdermal patch of the invention will deliver a partially or fully antagonizing dose of naltrexone which imparts safety from fentanyl or opioid analgesic over-dose, which can result in death, and reduces the rewarding effect, i.e., a "drug-liking" or euphoric effect, that is craved by drug abusers. In this way, a transdermal patch of the invention provides sufficient release of naltrexone to reduce or eliminate "drug-liking" or euphoric effects of the abuse and offers a margin of safety resulting from full or partial antagonism of fentanyl. Advantageously, a transdermal patch of the invention provides a margin of safety against abuse but also against overdose and even death.

The drug-in-adhesive layer may contain about 0.05 to about 1.75 mg/cm$^2$ of fentanyl or an analog thereof; preferably about 0.07 to about 1.50 mg/cm$^2$ of fentanyl or an analog thereof; about 0.08 to about 1.25 mg/cm$^2$ of fentanyl or an analog thereof; about 0.09 to about 1.0 mg/cm$^2$ of fentanyl or an analog thereof; about 0.1 to about 0.75 mg/cm$^2$ of fentanyl or an analog thereof; or about 0.12 to about 0.5 mg/cm$^2$ of fentanyl or an analog thereof. For other mu opioid agonists, the drug-in-adhesive layer may contain an equianalgesic amount of a particular agonist as known in the art. The amount of 4:3 naltrexone: 5-methyl-2-furaldehyde cocrystal present in the drug-in-adhesive layer is an amount sufficient to at least reduce the "drug liking" impact of the drug abuse and/or to provide a partial or full blockade of the analgesic effect. The amount of 4:3 naltrexone: 5-methyl-2-furaldehyde cocrystal present in terms of the molar ratio of naltrexone to fentanyl or an analog thereof, or other mu opioid agonist used, may range from about 0.075:1 to about 30:1, about 0.25:1 to about 20:1, about 0.5:1 to about 16:1, about 0.5:1 to about 14:1, about 0.75:1 to about 12:1, about 1:1 to about 10:1, about 1.5:1 to about 8:1, about 2:1 to about 6:1, and about 2:1 to about 4:1, or about 1:1 to about 4:1.

As discussed above, the adhesive used in the drug-in-adhesive layer may be a standard pressure sensitive adhesive known in the art or mixtures thereof. The adhesive polymer matrix and its method of preparation should be selected such that it is compatible with fentanyl or the fentanyl analog used and such that the crystalline form of the 4:3 naltrexone: 5-methyl-2-furaldehyde cocrystal is maintained. The adhesive polymer matrix is formulated to control the release of the drug from the patch and its permeation through the skin. As known in the art, the adhesive polymer matrix may also contain plasticizers or tackifiers that modify the rheology and adhesion characteristics of the adhesive, and may additionally include a chemical permeation enhancer such as alcohols, fatty acids, and esters to modify the rate of drug penetration through the skin. The drug-in-adhesive layer may optionally contain additional components, such as additives, stabilizers, dyes, diluents, pigments, carriers, inert fillers, antioxidants, excipients, gelling agents, anti-irritants, vasoconstrictors, and other materials as are generally known to the transdermal art.

A drug-in-adhesive transdermal patch of the invention may be manufactured using methods known in the art. The 4:3 naltrexone: 5-methyl-2-furaldehyde cocrystal particles may be incorporated into the drug-in-adhesive layer also using known methods such as melt blending. The 4:3 naltrexone: 5-methyl-2-furaldehyde cocrystal particles may be dispersed in a liquid in which the cocrystal is not soluble or only sparingly soluble (a "non-solvent") and then added to a solution of the other drug-in-adhesive layer components in that same liquid. Alternatively, the 4:3 naltrexone: 5-methyl-2-furaldehyde cocrystal particles may be dispersed into the solution of the drug-in-adhesive components itself. Use of a non-solvent ensures that the cocrystal retains its crystalline form while forming the drug-in-adhesive layer. For the 4:3 naltrexone: 5-methyl-2-furaldehyde cocrystal, such a liquid will generally be a non-polar organic solvent. An example of such a solvent is heptane in which the 4:3 naltrexone: 5-methyl-2-furaldehyde cocrystal has a solubility of only 0.1 mg/mL at 5° C. and of 0.2 mg/mL at 50° C. Alternatively, the 4:3 naltrexone: 5-methyl-2-furaldehyde cocrystal particles may be incorporated into the drug-in-adhesive layer also using known methods such as melt blending.

The invention further relates to a method of treating pain, such as acute, chronic, or intermittent pain, by applying a drug-in-adhesive transdermal patch according to the invention to the skin of a patient in need thereof. Accordingly, the invention relates to the use of a drug-in-adhesive transdermal patch to treat pain in a patient in need thereof. Patients should apply a transdermal patch of the invention to intact, non-irritated, and non-irradiated skin on a flat surface such as the chest, back, flank, or upper arm. A transdermal patch of the invention is typically worn for up to 72 hours.

As discussed above, transdermal patches are used in the art to administer fentanyl or an analog thereof to treat pain as well as to administer other mu opioid agonists. Transdermal patches, generally speaking, are either a drug-in-adhesive style (discussed above) or a reservoir style. In a reservoir style transdermal patch, the drug to be delivered is contained in a reservoir portion with a membrane between placed between the drug reservoir and the skin. The membrane controls the release rate of drug to the skin. As known in the art, a reservoir-style transdermal patch typically has a backing layer, a drug reservoir portion, a membrane, an adhesive, and a release sheet, which is removed from the patch to expose the adhesive when applying the patch to the skin. The transdermal analgesic system disclosed in U.S. Pat. Nos. 8,440,220 B2 and 8,747,889 B2, discussed above, are examples of reservoir style transdermal patches. In those reservoir transdermal patches, the analgesic and antagonist layers are contained in distinct reservoir layers separated by an impermeable barrier layer and the antagonist is to release only is situations of misuse or abuse.

In another embodiment, the invention relates to an improvement in transdermal patches used to administer fentanyl or an analog thereof or another mu opioid agonist. The invention combines in a transdermal patch an effective amount of a 4:3 naltrexone: 5-methyl-2-furaldehyde cocrystal as an opioid antagonist to provide a tamper-resistant or abuse-deterrent transdermal patch. Accordingly, the invention relates to an improved transdermal patch for administering fentanyl or an analog thereof, or for administering a mu opioid agonist, the improvement wherein the transdermal patch contains a 4:3 naltrexone: 5-methyl-2-furaldehyde cocrystal in an abuse limiting amount such as those amounts discussed above. The improved transdermal patch may any transdermal patch type known in the art, including but not limited to a drug-in-adhesive transdermal patch or a reservoir transdermal patch.

EXAMPLES

The following analytical methods were used to characterize the 4:3 naltrexone: 5-methyl-2-furaldehyde cocrystals of the invention:

X-ray Powder Diffraction (XRPD) Characterization:

XRPD analysis was carried out on a Panalytical X'pert pro, scanning the samples between 3 and 35° 2θ. Material, approximately 10 mg, was gently ground and loaded onto a multi well plate with Kapton or mylar polymer film to support the sample. The multi well plate was then loaded into a Panalytical diffractometer running in transmission mode and analysed, using the experimental conditions described in Table 1.

TABLE 1

| Raw Data Origin: | XRD measurement (*.XRDML) |
|---|---|
| Scan Axis: | Gonio |
| Start Position [°2θ]: | 3.0066 |
| End Position [°2θ]: | 34.9866 |
| Step Size [°2θ]: | 0.0130 |
| Scan Step Time [s]: | 18.8700 |
| Scan Type: | Continuous |
| PSD Mode: | Scanning |
| PSD Length [°2θ]: | 3.35 |
| Offset [°2θ]: | 0.0000 |
| Divergence Slit Type: | Fixed |
| Divergence Slit Size [°]: | 1.0000 |
| Measurement Temperature [° C.]: | 25.00 |
| Anode Material: | Cu |
| K-Alpha1 [Å]: | 1.54060 |
| K-Alpha2 [Å]: | 1.54443 |
| K-A2/K-A1 Ratio: | 0.50000 |

TABLE 1-continued

| Generator Settings: | 40 mA, 40 kV |
|---|---|
| Goniometer Radius [mm]: | 240.00 |
| Dist. Focus-Diverg. Slit [mm]: | 91.00 |

Single Crystal X-Ray Diffraction (SXD) Characterization:

Diffraction data from a single crystal was collected with Cu-Kα radiation (λ=1.54184 Å) at 120 K on an Agilent Supernova dual-source diffractometer equipped with an Oxford Cryosystems low temperature device. Data were integrated and a multiscan correction for systematic errors applied (CRYSALISPRO). The structure was solved by charge flipping (Superflip) and refined against $F^2$ using all data (ShelxL-2014).

Polarised Light Microscopy (PLM):

The presence of crystallinity (birefringence) was determined using an Olympus BX50 polarising microscope, equipped with a Motic camera and image capture software (Motic Images Plus 2.0).

Thermogravimetric Analysis (TGA):

Approximately 10 mg of material was weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 $cm^3$/min.

Differential Scanning Calorimetry (DSC):

Approximately 5 mg of material was weighed into an aluminium DSC pan and sealed nonhermetically with a pierced aluminium lid. The sample pan was then loaded into a Seiko DSC6200 (equipped with a cooler) cooled and held at 25° C. Once a stable heat-flow response was obtained, the sample and reference were heated to 220° C. at scan rate of 10° C./min and the resulting heat flow response monitored.

$^1$H-Nuclear Magnetic Resonance Spectroscopy ($^1$H-NMR):

$^1$H-NMR experiments were performed on a Bruker pr500 (frequency: 500 MHz). Experiments were performed in deuterated DMSO and each sample was prepared to an approximate 10 mM concentration.

Dynamic Vapor Sorption (DVS):

Approximately 10 mg of sample was placed into a mesh vapor sorption balance pan and loaded into a Hiden IGAsorp by Hiden. The sample was subjected to a ramping profile from 40-90% relative humidity (RH) at 10% increments, maintaining the sample at each step until a stable weight had been achieved (99.5% step completion). After completion of the sorption cycle, the sample was dried using the same procedure to 0% RH the sample was then subsequently taken back to 40% RH using the same procedure.

Infrared Spectroscopy (IR):

Infrared spectroscopy was carried out on a Bruker ALPHA P spectrometer. Sufficient material was placed onto the centre of the plate of the spectrometer and the spectra were obtained using the parameters in Table 2:

TABLE 2

| Resolution: | 4 $cm^{-1}$ |
|---|---|
| Background Scan Time: | 16 scans |
| Sample Scan Time: | 16 scans |
| Data Collection: | 4000 to 400 $cm^{-1}$ |

TABLE 2-continued

| Result Spectrum: | Transmittance |
| --- | --- |
| Software: | OPUS version 6 |

Example 1

4:3 Naltrexone: 5-methyl-2-furaldehyde Cocrystal

1.1 Preparation of a 4:3 Naltrexone: 5-methyl-2-furaldehyde Cocrystal by Grinding 492 mg of naltrexone monohydrate (1.369 mmoles) were ground with 381 μl of 5-methyl-2-furaldehyde (3.83 mmoles) until a dry and homogenous powder was obtained at room temperature, 22° C.

1.1.1 XRPD Characterization 4:3 Naltrexone: 5-methyl-2-furaldehyde Cocrystal The experimental XRPD pattern of the 4:3 naltrexone: 5-methyl-2-furaldehyde cocrystal prepared by grinding in Example 1.1 is shown in FIG. 1. Table 3 lists the angles, °2θ±0.2 °2θ and d spacing of the peaks identified in the experimental XRPD pattern of FIG. 1. The entire list of peaks, or a subset thereof, may be sufficient to characterize the co crystal, as well as by an XRPD pattern similar to FIG. 1. For example, a 4:3 naltrexone: 5-methyl-2-furaldehyde cocrystal of the invention may be characterized by a powder X-ray diffraction pattern having at least peaks selected from 11.5, 13.1, and 17.5 °2θ±0.2 °2θ.

TABLE 3

| Angle °2θ ± 0.2°2Θ | d Value Angstrom (Å) | Intensity % |
| --- | --- | --- |
| 3.6 | 24.33 | 1.6 |
| 6.5 | 13.69 | 4.6 |
| 7.2 | 12.27 | 48.9 |
| 7.3 | 12.05 | 100.0 |
| 7.9 | 11.25 | 8.9 |
| 8.3 | 10.67 | 6.7 |
| 8.9 | 9.98 | 2.0 |
| 9.5 | 9.31 | 2.1 |
| 10.1 | 8.79 | 5.4 |
| 10.1 | 8.73 | 6.7 |
| 10.8 | 8.17 | 5.6 |
| 11.1 | 7.99 | 1.2 |
| 11.5 | 7.67 | 10.9 |
| 11.9 | 7.45 | 26.2 |
| 12.4 | 7.11 | 50.8 |
| 12.6 | 7.03 | 28.1 |
| 13.1 | 6.77 | 62.4 |
| 13.6 | 6.51 | 3.4 |
| 14.4 | 6.14 | 22.5 |
| 14.7 | 6.02 | 13.4 |
| 15.3 | 5.79 | 18.6 |
| 15.5 | 5.71 | 1.6 |
| 15.9 | 5.56 | 30.6 |
| 17.0 | 5.22 | 32.5 |
| 17.5 | 5.08 | 31.5 |
| 17.9 | 4.96 | 6.5 |
| 18.0 | 4.91 | 14.8 |
| 18.8 | 4.72 | 17.7 |
| 19.1 | 4.65 | 28.7 |
| 19.5 | 4.55 | 19.0 |

1.1.2 Polarized Light Microscopy Characterization of the 4:3 Naltrexone 5-methyl-2-furaldehyde cocrystal Polarized light microscopy characterization of the 4:3 naltrexone: 5-methyl-2-furaldehyde cocrystal showed a birefringent material with very small particle size (c.a<5 μm) having a needle like morphology.

Figure 2:
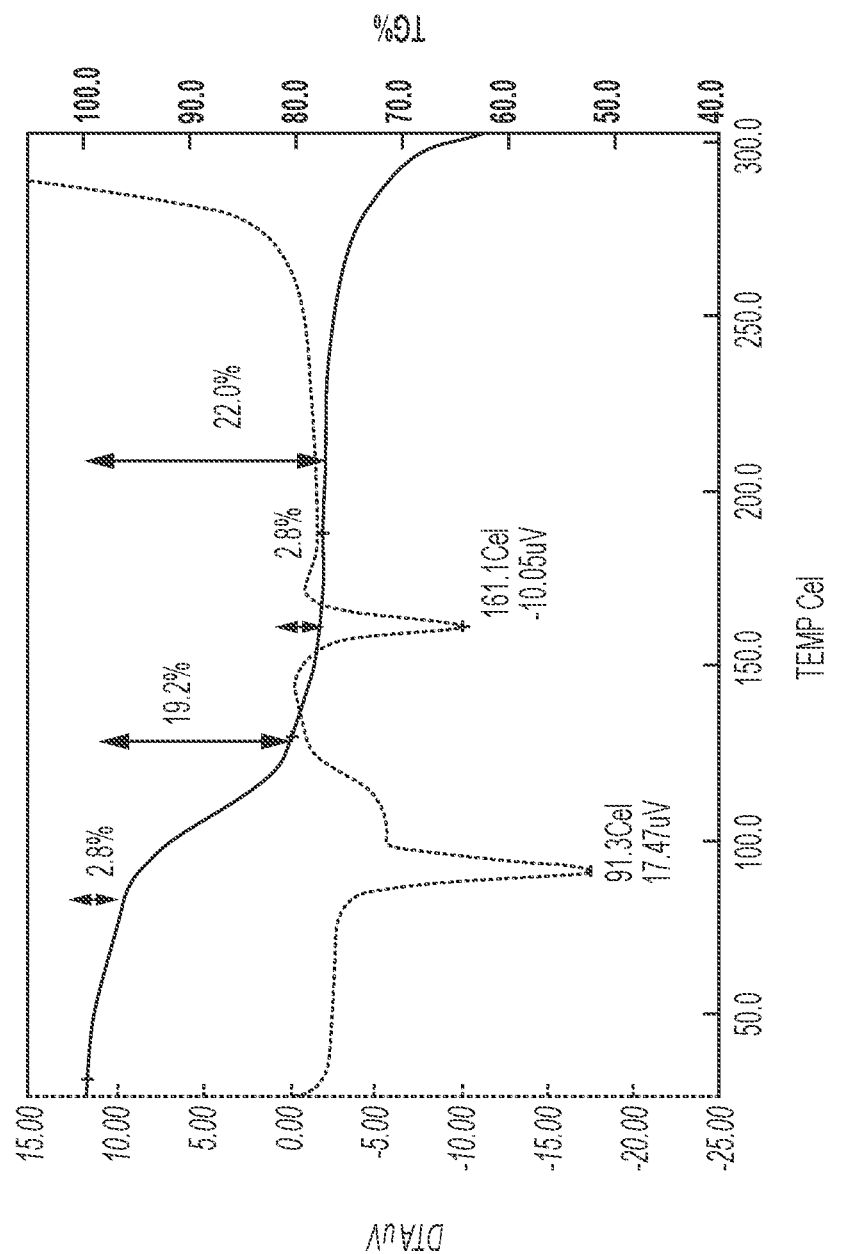
FIG. 2 is the TG/DTA trace for the Naltrexone: 5-methyl-2-furaldehyde cocrystal prepared by grinding in Example 1.1.

1.1.3 Thermal Gravimetric Analysis of the 4:3 Naltrexone: 5-methyl-2-furaldehyde cocrystal The thermal gravimetric analysis trace, FIG. 2, shows a slight weight loss observed between 25-75° C. (TGA), not detected by DT due to unbound 5-methyl-2-furaldehyde and corresponding to 2.8% of mass loss. Then a loss of mass of 19.2% with associated endotherms must be associated with the loss of lattice bounded 5-methyl-2-furaldehyde between 75-250° C. As seen in the single crystal structure, Example 1.2.1 below, the stoichiometry is of 3 moles of 5-methyl-furfural to 4 moles naltrexone molecule. This should give a loss of weight of 19.47% which is very close to the weight loss bserved. Subsequent to this weight loss, a crystallisation (exotherm) with loss of weight occurs at temperature higher than 250° C. and is most likely to be decomposition.

Figure 3:
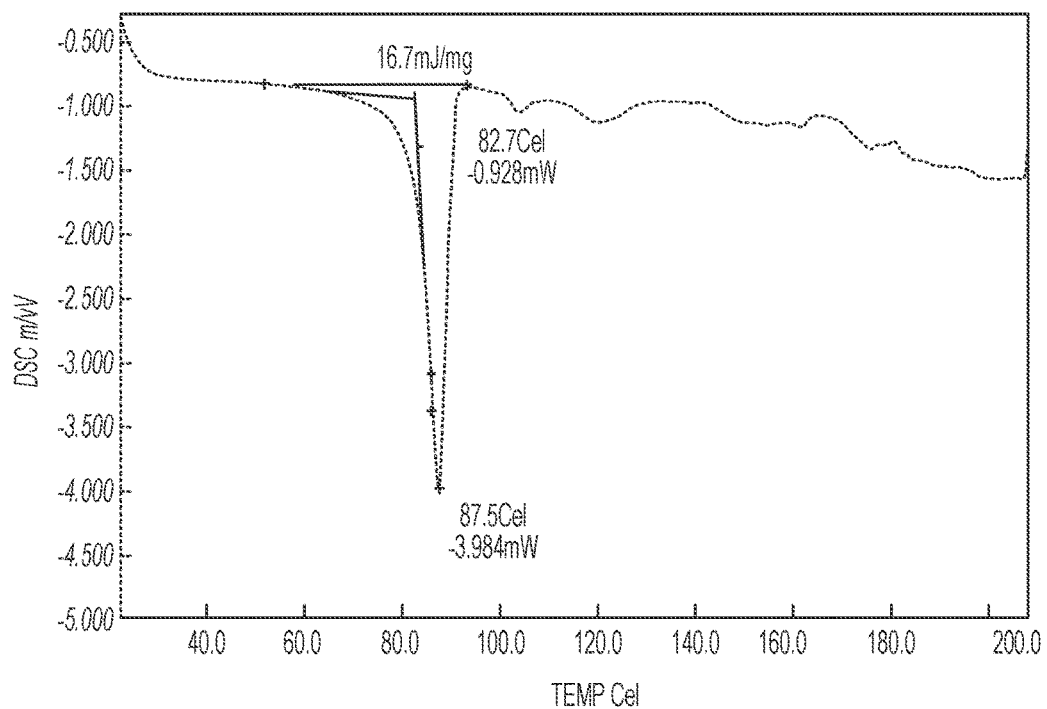
FIG. 3 is the DSC trace for the Naltrexone: 5-methyl-2-furaldehyde cocrystal prepared by grinding in Example 1.1.

1.1.4 Differential Scanning Calorimetry (DSC) Analysis of the 4:3 Naltrexone: 5-methyl-2-furaldehyde cocrystal The DSC trace, FIG. 3, shows a single endotherm with an onset at 82.7° C. and a peak maximum at 87.5° C.

Figure 4:
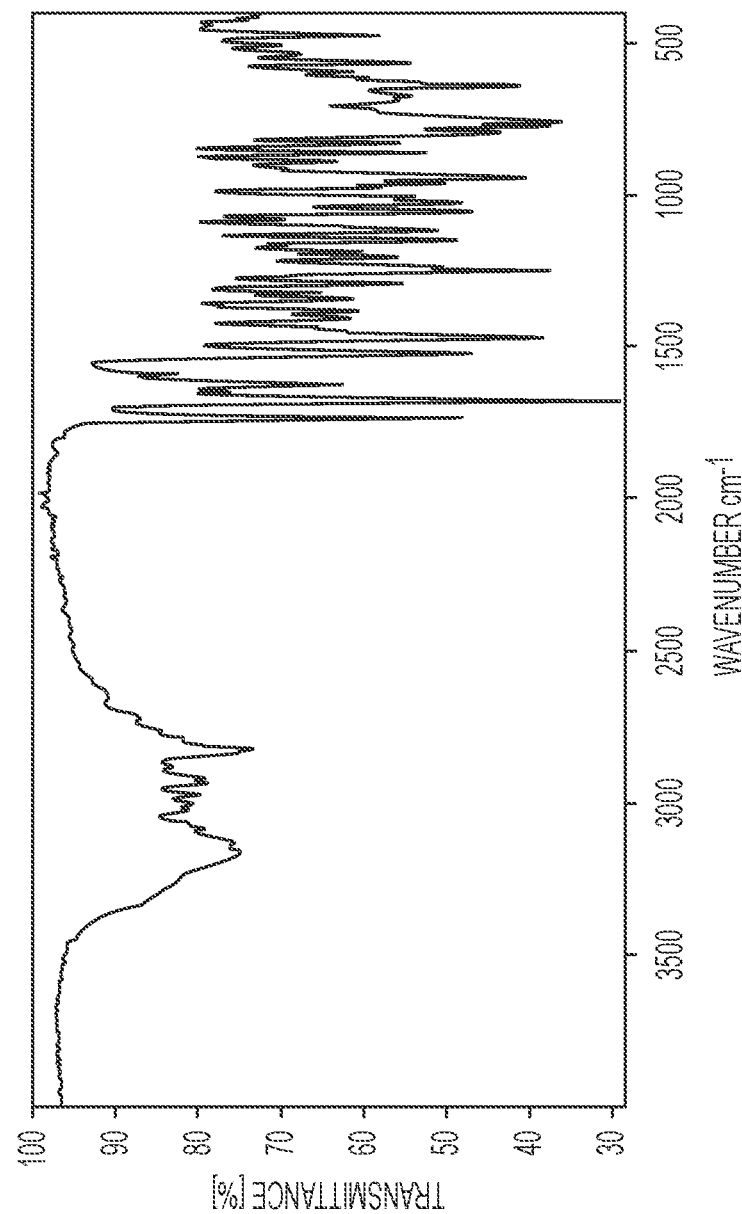
FIG. 4 depicts the FTIR spectrum of the Naltrexone: 5-methyl-2-furaldehyde cocrystal prepared by grinding in Example 1.1.

1.1.5 FTIR Characterization of 4:3 Naltrexone: 5-methyl-2-furaldehyde cocrystal The FTIR spectra, FIG. 4, of 4:3 naltrexone: 5-methyl-2-furaldehyde cocrystal clearly shows the I.R. absorption band of the naltrexone ketone at 1727 cm$^{-1}$ and the I.R. absorption band of the aldehyde group from the 5-methyl-2-furaldehyde at 1671 cm$^{-1}$.

Figure 5:
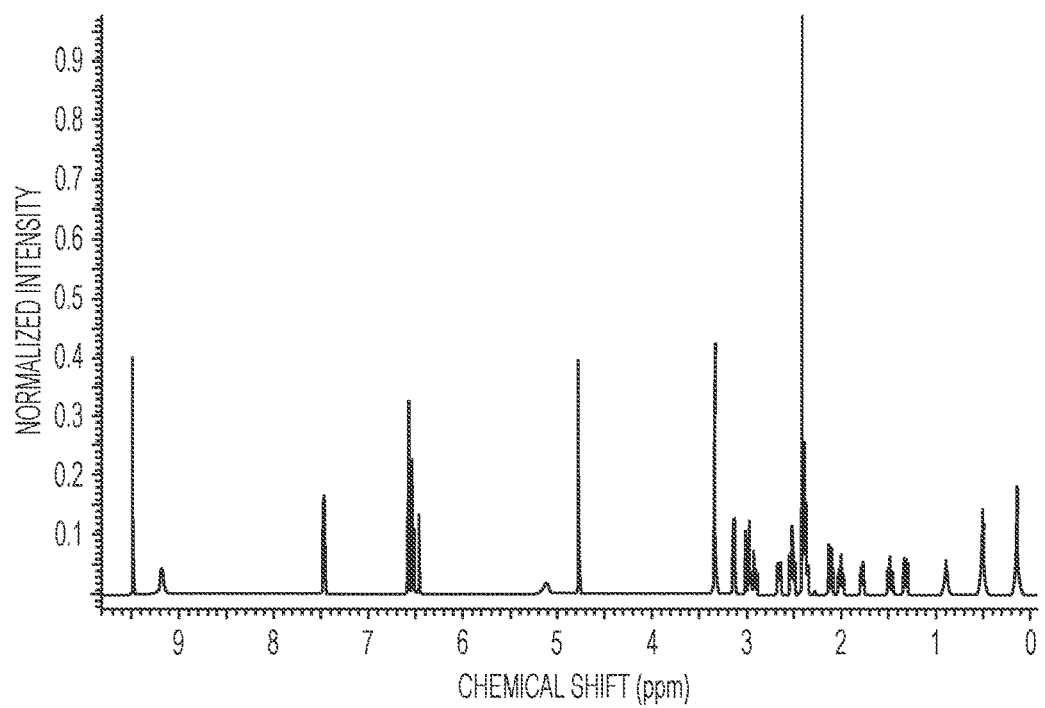
FIG. 5 depicts the $^1$H NMR spectrum of the Naltrexone: 5-methyl-2-furaldehyde cocrystal prepared by grinding in Example 1.1.

1.1.6 $^1$H NMR Spectrum of 4:3 Naltrexone: 5-methyl-2-furaldehyde cocrystal The $^1$H NMR spectrum of the 4:3 naltrexone: 5-methyl-2-furaldehyde cocrystal shown in FIG. 5, displays the following peaks: $^1$H NMR (500 MHz, d6-DMSO) δ: 9.48 (0.75H), 9.18 (1H), 7.46 (0.75H), 6.56 (2H), 6.45 (0.75H), 5.11 (1H), 4.77 (1H), 3.13 (1H), 2.91 (2H), 2.64 (1H), 2.51 (1H), 2.37 (5.75H), 2.11 (1H), 2.00 (1H), 1.76 (1H), 1.48 (1H), 1.33 (1H), 0.88 (1H), 0.5 (2H), 0.14 (2H).

Figure 6:
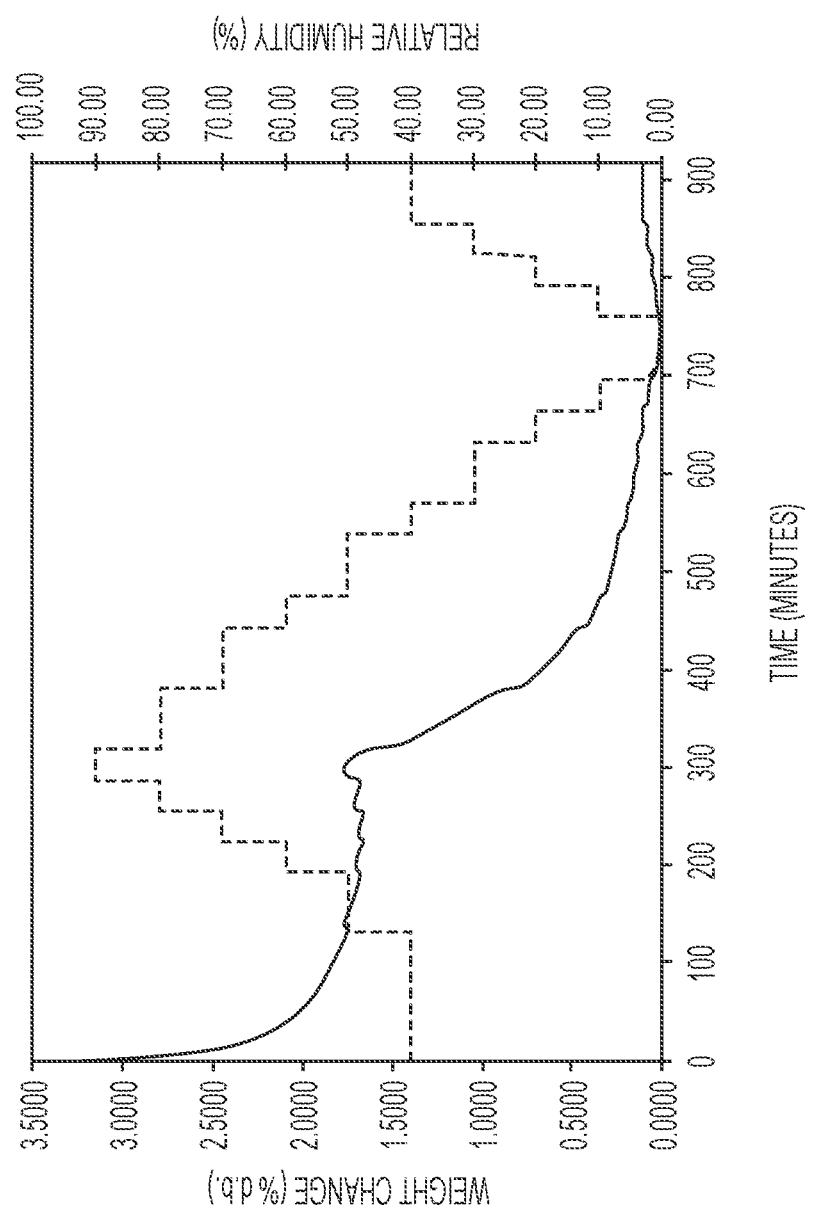
FIG. 6 depicts the DVS trace of the Naltrexone: 5-methyl-2-furaldehyde cocrystal prepared by grinding in Example 1.1.

1.1.7 Dynamic Vapor Sorption (DVS) Analysis for 4:3 Naltrexone: 5-methyl-2-furaldehyde cocrystal A DVS analysis of the 4:3 naltrexone: 5-methyl-2-furaldehyde cocrystal was performed using Hiden IGAsorp method. The DVS kinetic analysis showed the 4:3 naltrexone: 5-methyl-2-furaldehyde cocrystal, see FIG. 6, to be not hygroscopic as the mass change is less 3% and the powder pattern for the material reclaimed after the experiment has the same XRPD pattern as in FIG. 1.

1.2 Solution Preparation of the 4:3 Naltrexone: 5-methyl-2-furaldehyde Cocrystal 30 mg (0.083 mmoles) naltrexone monohydrate was dissolved in 3 ml of acetonitrile and 50 μl of 5-methyl-2-furaldehyde (0.502 mmoles) were added and the acetonitrile allowed to slowly evaporate over 18 hours at room temperature leaving a mixture of crystalline solids. A single crystal suitable for single crystal x-ray characterization was isolated from the mixture and used.

1.2.1 Single Crystal X-Ray Diffraction (SXD) Characterization of the 4:3 Naltrexone: 5-methyl-2-furaldehyde Cocrystal SXD characterization of the crystal prepared and isolated in Example 1.2 showed it to be a 4:3 naltrexone: 5-methyl-2-furaldehyde cocrystal. The single crystal data and refinement parameters for the structure measured at 120K are reported in Table 4, below.

TABLE 4

| Molecular formula | $C_{98}H_{110}N_4O_{22}$ |
| --- | --- |
| Molecular weight | 1695.98 |
| Crystal system | Orthorhombic |
| Space group | $P2_12_12_1$ |
| Unit cell dimensions | a = 12.5936(5) Å; $\alpha = 90°$ |
|  | b = 13.9816(6) Å; $\beta = 90°$ |
|  | c = 47.6259(18) Å; $\gamma = 90°$. |
| Cell volume | 8385.9(6) Å3 |
|  | Z = 4 |
| Temperature | 120(2) K |
| Radiation wave length | Cu-K$\alpha$, $\lambda$ = 1.54184 A |
| Goodness of fit | 1.039 |
| R factor | 0.0592 |
| Morphology | needle |

Figure 7:
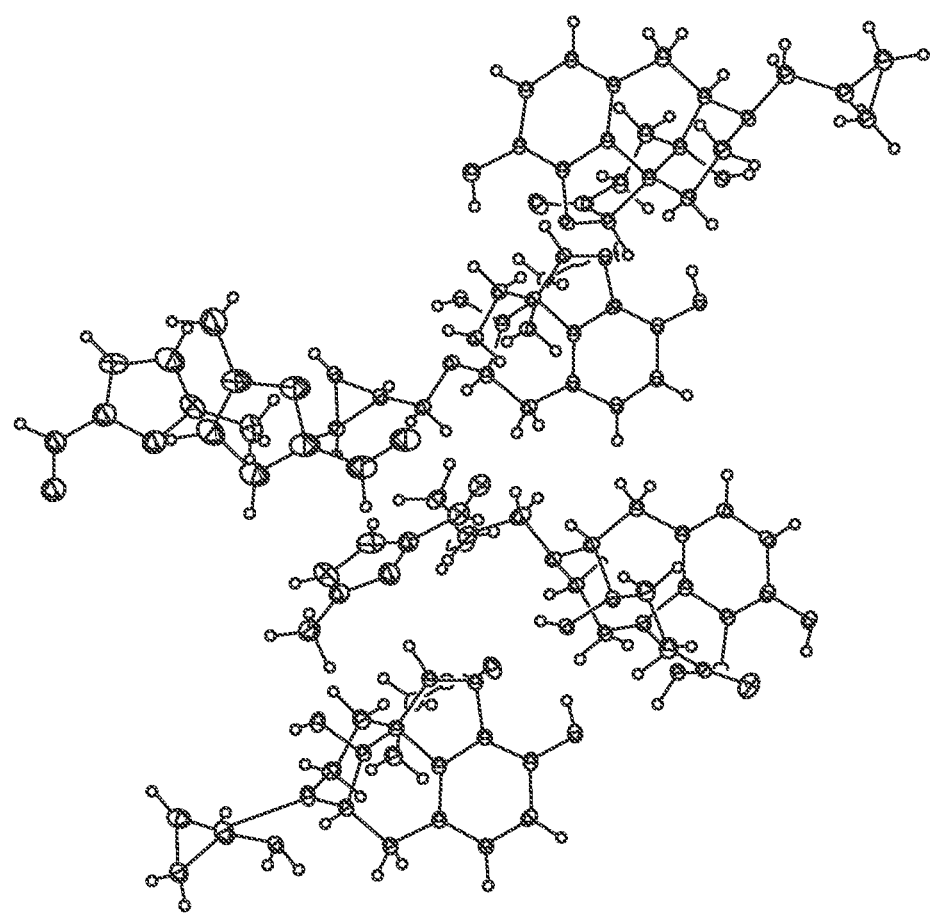
FIG. 7 depicts the structure of the 4:3 naltrexone: 5-methyl-2-furaldehyde cocrystal in Example 1.2 by single crystal X-ray diffraction (SXD) at 120K.
Figure 8:
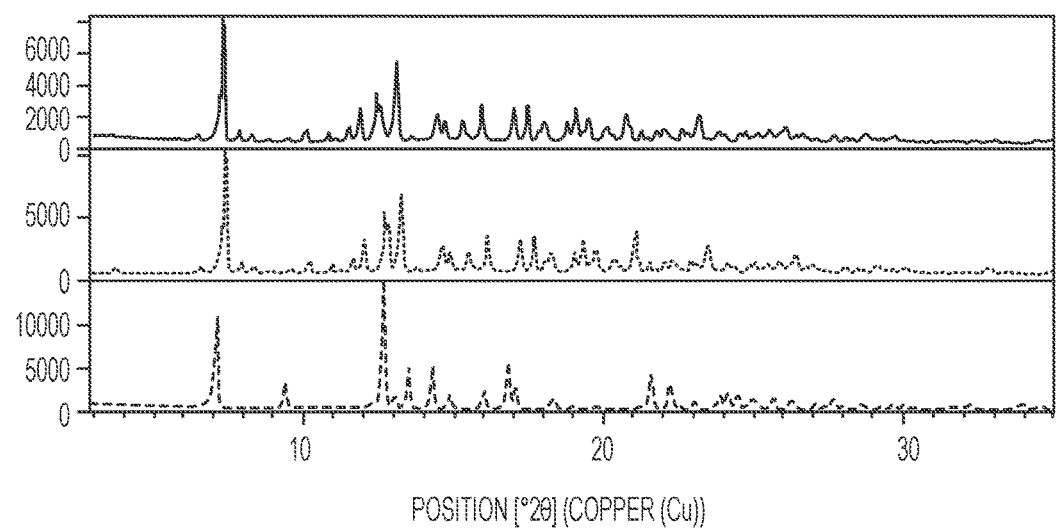
FIG. 8 depicts the XRPD patterns of the cocrystal prepared in Example 1.1 (red, top), a simulated XRPD pattern from the single crystal structure at 120K in Example 1.2 (green, middle) and naltrexone monohydrate (blue, bottom).

An ORTEP diagram of the 4:3 naltrexone: 5-methyl-2-furaldehyde cocrystal at 120K showing the assymetric unit is in FIG. 7. The SXD characterization showed the 4:3 stoichiometry of the naltrexone: 5-methyl-2-furaldehyde cocrystal. Anisotropic atomic displacement ellipsoids for non-hydrogen atoms are shown at the 30% probability level. The calculated XRPD pattern based on the single crystal data and structure of the 4:3 naltrexone: 5-methyl-2-furaldehyde cocrystal at 120K is shown in FIG. 3. It is to be noticed there are small shifts in some of the peak positions owing to the fact the experiment al powder pattern XRPD was collected at room temperature and the calculated XRPD pattern is derived from data collected at 120K. There are also small intensity differences owing to preferred orientation effects, present in the experimental pattern. FIG. 8 is a stack of XRPD patterns of the XRPD obtained from the cocrystal prepared in Example 1.1 (red, top), a simulated XRPD pattern from the single crystal structure at 120K (green, middle), and the XRPD pattern naltrexone monohydrate (blue, bottom).

Example 2

Drug-in-Adhesive Transdermal Patch with Fentanyl as the API

A drug-in-adhesive patch according to the invention may be manufactured by the following process:
1. Disperse fentanyl in a medical-grade silicone such as Dow-Corning 360 Medical Fluid, a linear polydimethylsiloxane (PDMS) having a viscosity of 100 cSt.
2. Dissolve a pressure sensitive adhesive (PSA) such as Dow Bio PSA 7-4201 in heptane or another non-polar solvent. Dow Bio PSA 7-4201 is an amine-compatible silicone pressure sensitive adhesive which dissolves in solvents (heptane) specifically designed for pharmaceutical use. Dow Bio PSA's are designed to adhere transdermal drug delivery systems (TDDS) to the skin and show enhanced chemical stability in the presence of amine-functional drugs, excipients, and enhancers.
3. Add the fentanyl dispersion to the PSA/heptane solution to form a mixture.
4. Disperse 4:3 naltrexone: 5-methyl-2-furaldehyde cocrystal into the mixture.
5. Coat the mixture coated onto a release liner such as 3M 1022 release liner and dried release-side up to form a film. The drying may be done at elevated temperature as is known in the art, e.g., about 78° C.
6. The film is then laminated onto a backing layer such as 3M Scotchpak™ 1012 polyester film laminate backing layer and cut to size.

Figure 10A:
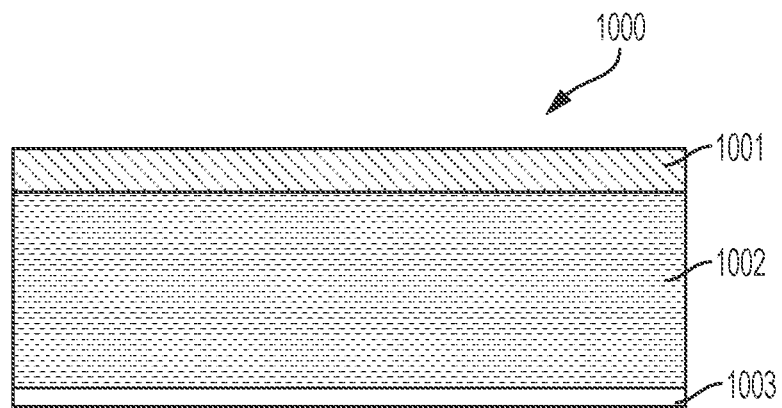
FIGS. 10a and 10b depict a drug-in-adhesive transdermal patch as described in Example 2.
Figure 10B:
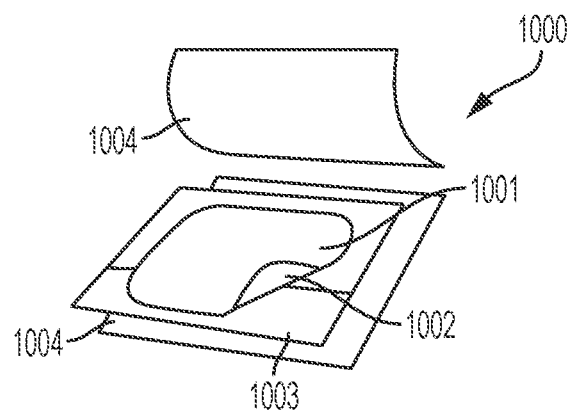

A non-polar solvent such as hexane is used because the 4:3 naltrexone: 5-methyl-2-furaldehyde cocrystal (NTX-Co) is sparingly soluble or insoluble in the solvent and thus retains its crystalline form. A transdermal patch of the invention may deliver 25 mcg/h of fentanyl or another API and be cut to a size of 6.25 cm². FIGS. 10a and 10b depict a drug-in-adhesive transdermal patch as described in this Example. The drug-in-adhesive transdermal patches [1000] depicted in FIGS. 10a and 10b have a backing layer [1001], a pressure sensitive adhesive layer [1002] which contains fentanyl and the 4:3 naltrexone: 5-methyl-2-furaldehyde cocrystal and is disposed on the backing layer, and a release layer [1003] disposed on the pressure sensitive adhesive layer [1002] opposite the backing layer [1001]. In FIG. 10b, the release layer [1003] also serves as a protective liner and the drug-in-adhesive transdermal patch [1000] is packaged between protective film layers [1004].

Example 3

Drug-in-Adhesive Transdermal Patch Model System

3.1 Preparation of the Transdermal Patch

A drug-in-adhesive transdermal patch was manufactured as described in Example 2, except that lidocaine was used as a surrogate API instead of fentanyl. Table 5 reports the composition of the drug-in-adhesive layer of the patch. Multiple 0.785 cm² patches were prepared for the dissolution and skin permeability testing described below.

TABLE 5

| Component | Amount (g) | Percent w/w |
| --- | --- | --- |
| Lidocaine (free base) | 0.100 | 3.47 |
| Dow-Corning 360 Medical Fluid (100 cSt) | 0.166 | 5.76 |
| Dow Bio PSA 7-4201 Silicone Adhesive | 2.230 | 77.38 |
| 4:3 naltrexone:5-methyl-2-furaldehyde cocrystal (NTX-Co) (451.41 g/mol) | 0.386 | 13.39 |
| Hexane | 4 mL | |

3.2 Dissolution Testing of the Transdermal Patch

Figure 11:
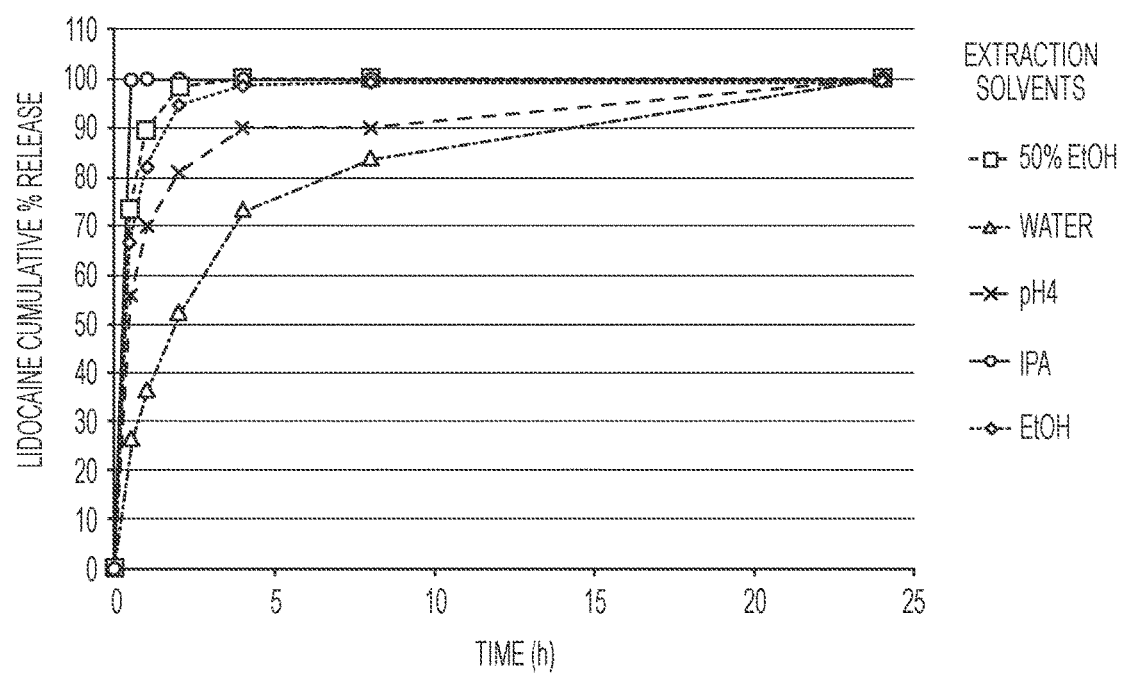
FIG. 11 depicts the dissolution profile of lidocaine, cumulative percentage released over time, in four solvents (water, 95% ethanol, 50/50 water/ethanol, and acidified water, pH 4) as described in Example 3.2.
Figure 12:
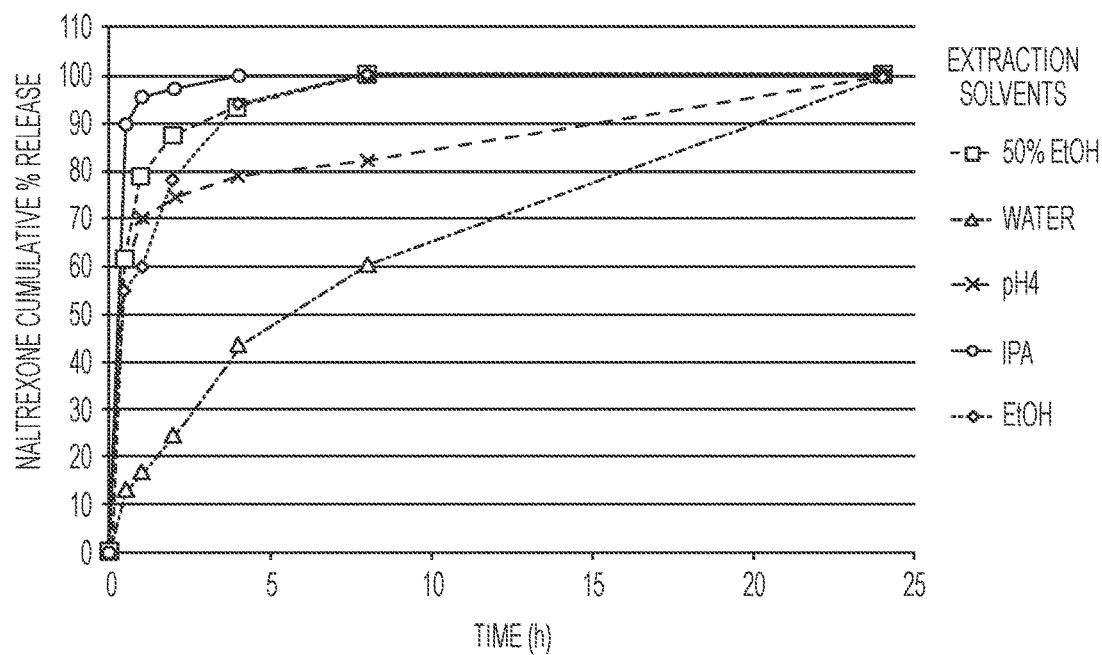
FIG. 12 depicts the dissolution profile of naltrexone, cumulative percentage released over time, in four solvents (water, 95% ethanol, 50/50 water/ethanol, and acidified water, pH 4) as described in Example 3.2.
Figure 13A:
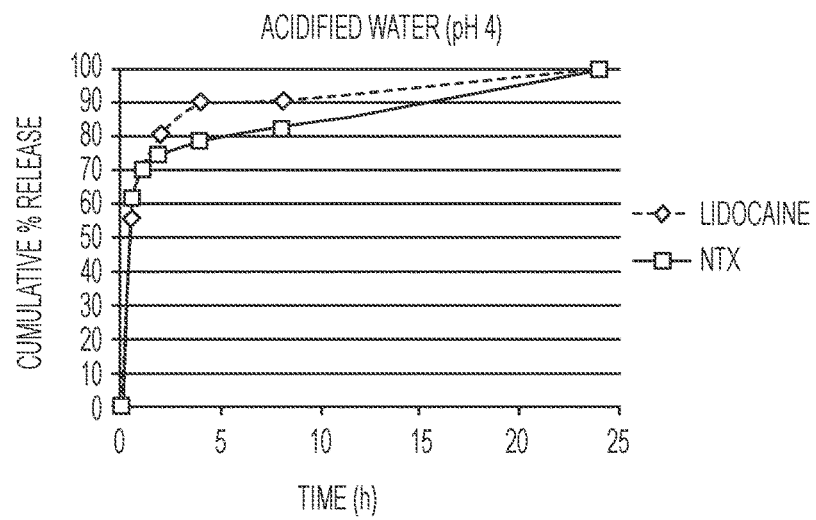
FIGS. 13a-e depict the comparative dissolution profile of lidocaine and naltrexone, cumulative percentage released over time, in four solvents (water, 95% ethanol, 50/50 water/ethanol, and acidified water, pH 4) as described in Example 3.2.
Figure 13B:
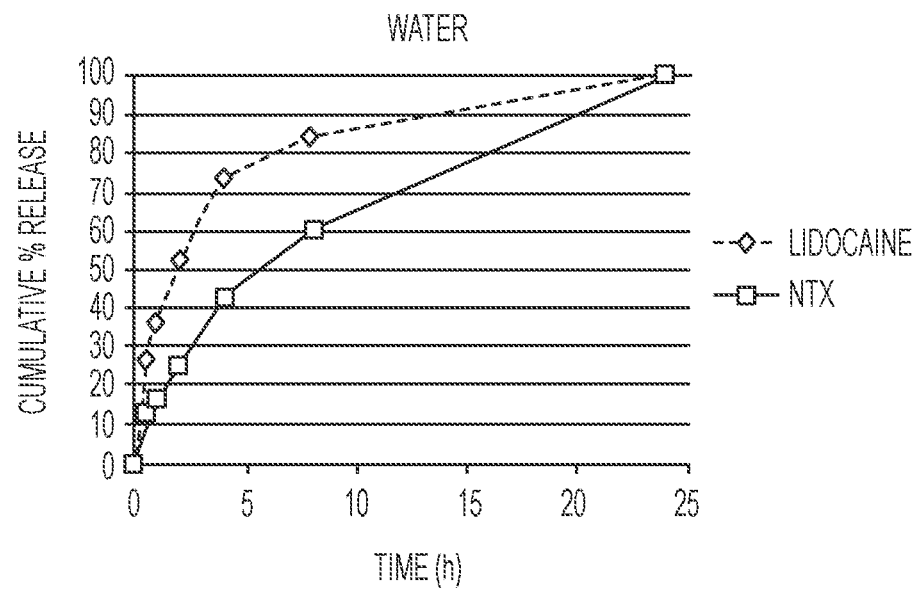
Figure 13C:
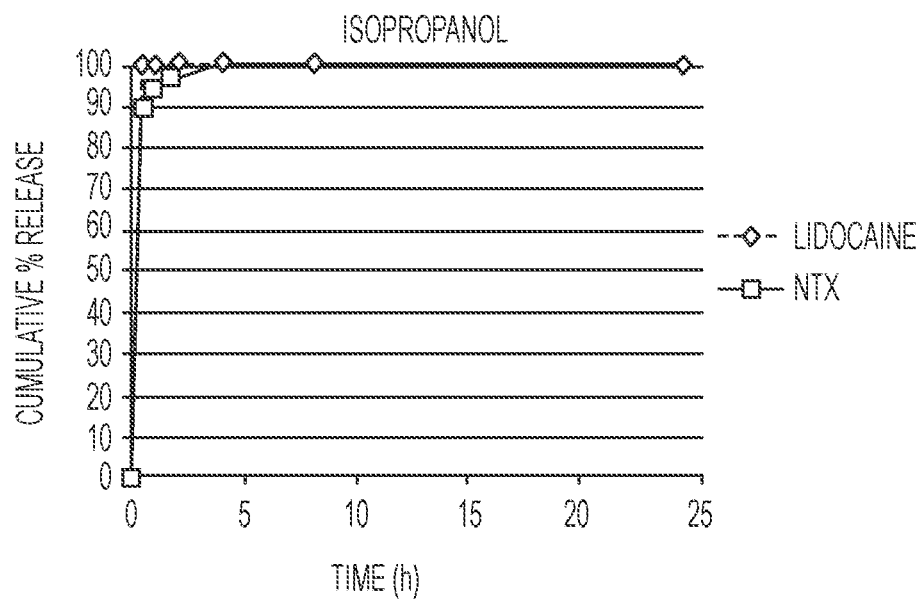
Figure 13D:
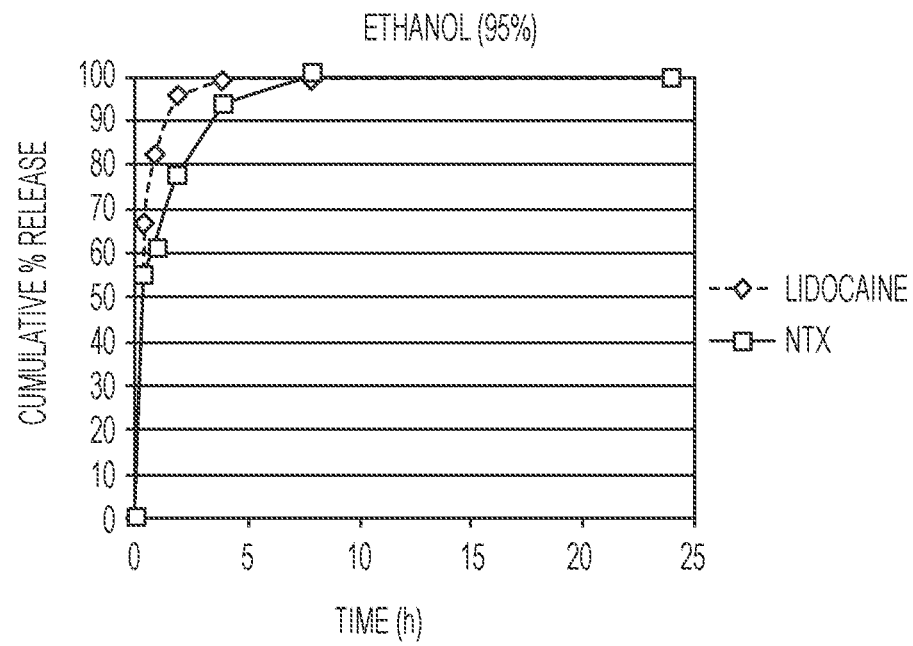
Figure 13E:
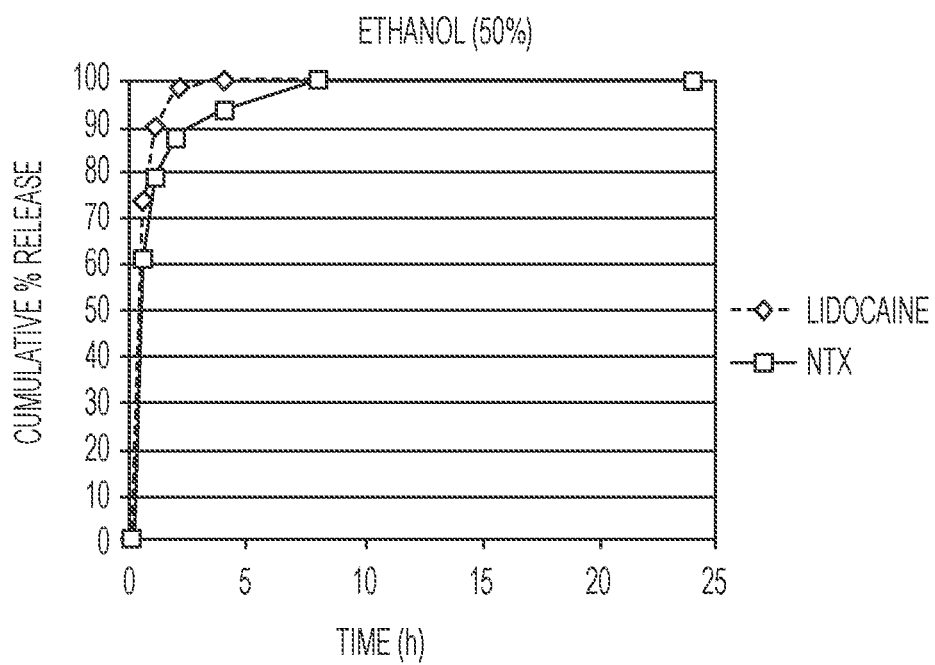

The release of the lidocaine API and naltrexone from the 4:3 naltrexone:5-methyl-2-furaldehyde cocrystal in the transdermal patch was studied using USP Type VII apparatus and dissolution methods in four solvents (water, 95% ethanol, 50/50 water/ethanol, and acidified water, pH 4) over 25 hours. HPLC was used to determine the concentration of lidocaine and naltrexone. Table 6 lists the HPLC methods and parameters. The HPLC analysis was run in duplicate (2 patches for each dissolution condition and reported as the average of the two runs. The results are shown in FIGS. 11-13. FIG. 11 shows the release profile of lidocaine, cumulative percentage released over time, in each solvent. FIG. 12 shows the dissolution profile of naltrexone, cumulative percentage released over time, in each solvent. FIGS. 13a-e show the comparative dissolution profile of lidocaine and naltrexone, cumulative percentage released over time, in each solvent. The data shows that the release rate of the naltrexone and the lidocaine are substantially similar or close to the same in all solvents. There is no selective release which might allow for abuse by separate extraction.

TABLE 6

| HPLC Methods and Parameters | |
|---|---|
| Naltrexone and Lidocaine | |
| Column | Agilent Eclipse Plus C-18 (L1) |
| Mobile Phase | 60:40 v/v 0.02M pH 5.8 ammonium acetate buffer:acetonitrile, isocratic |
| Flow Rate | 1.0 mL/min |
| Column Temp. | 30° C. |
| Detection λ | 206 nm |
| Injection Volume | 304 |
| Anticipated LOD | 1 µg/mL |
| Run Time | 20 min |

3.3 Skin Flux Evaluation

Figure 14:
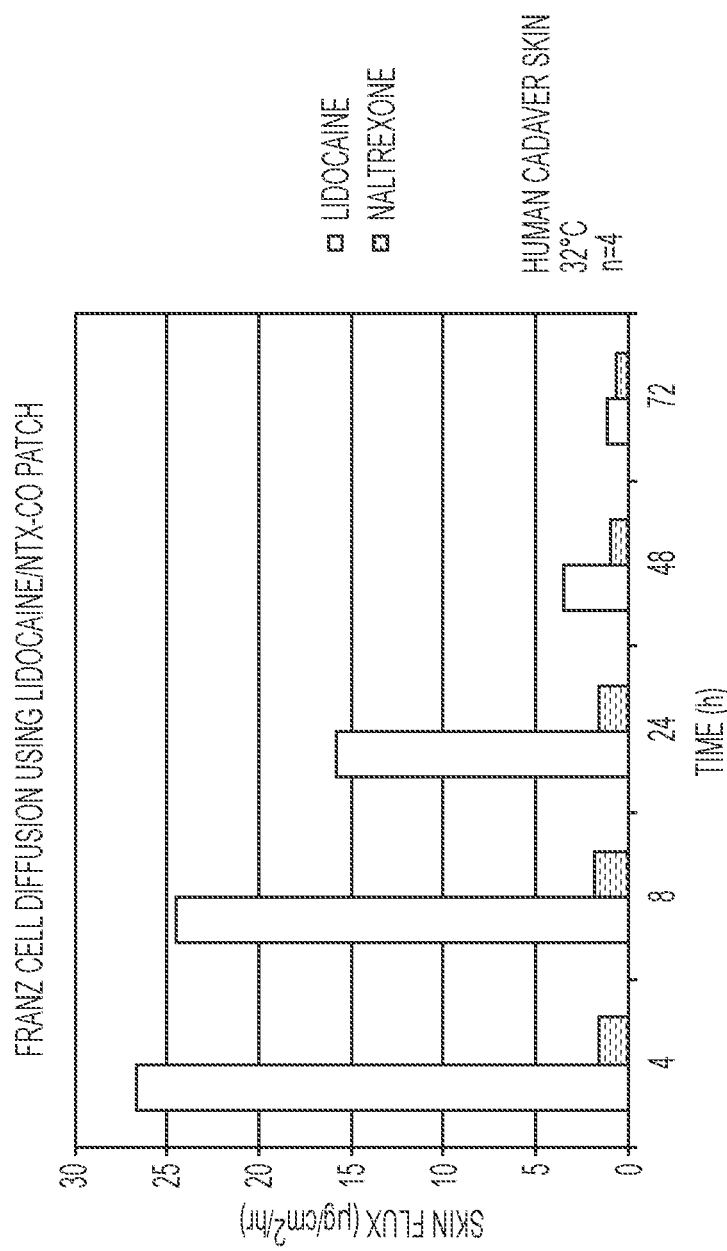
FIG. 14 depicts the Skin Flux ($\mu g/cm^2/hr$) of both liodocaine and naltrexone over a 72-hour period as described in Example 3.3.
Figure 15:
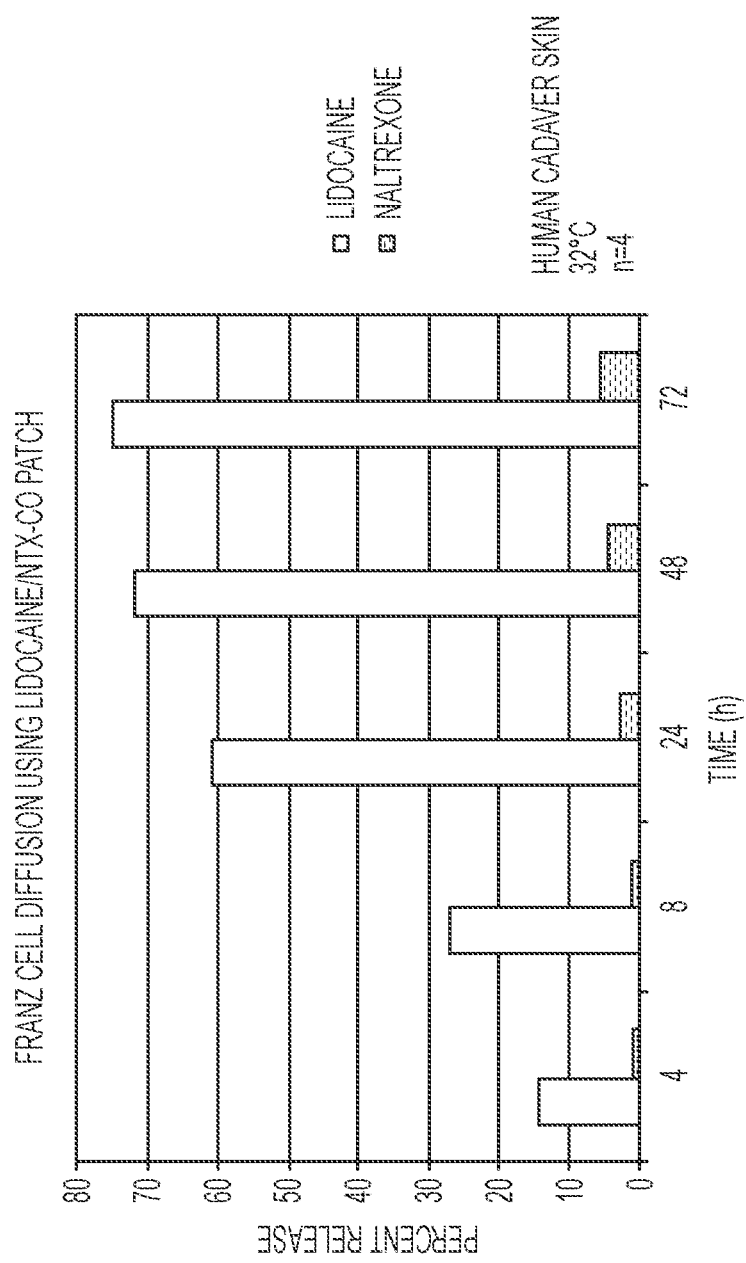
FIG. 15 depicts the percent release of both liodocaine and naltrexone over a 72-hour period as described in Example 3.3.
Figure 16:
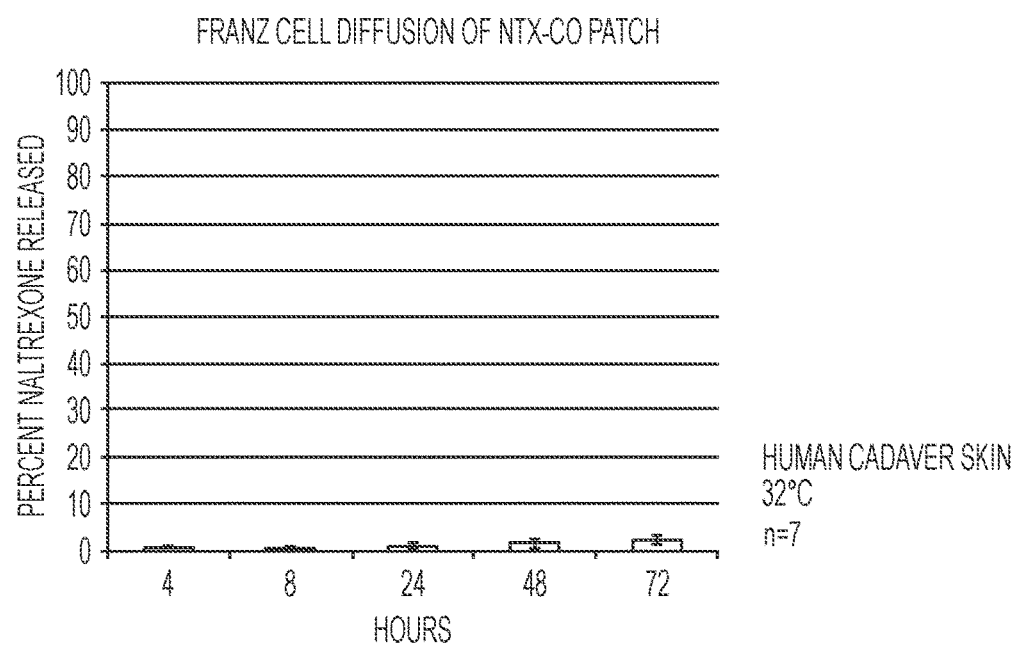
FIG. 16 depicts the the percent release of naltrexone from a transdermal patch containing only naltrexone: 5-methyl-2-furaldehyde cocrystal over a 72-hour period as described in Example 3.3.

The diffusion of lidocaine API and naltrexone from the 4:3 naltrexone: 5-methyl-2-furaldehyde cocrystal in the transdermal patch to the skin was studied using a Franz Cell Diffusion (FCD) method. In the method, transdermal patches were placed on top of heat-separated human cadaver skin. The receptor solution (0.01M phosphate buffer, pH 5.76) was analyzed for lidocaine and naltrexone content over time by HPLC using the methods discussed above. In one set of experiments the method used four transdermal patches (n=4) and was carried out at 32° C. The results for the n=4 experiments are shown in FIGS. 14 and 15. FIG. 14 shows the Skin Flux (µg/cm$^2$/hr) of both lidocaine and naltrexone over a 72-hour period. FIG. 15 shows the percent release of both lidocaine and naltrexone over a 72-hour period. In another set of experiments a similar film was prepared as above without lidocaine (Dow Medical Fluid 100-5%/Dow 7-4201-88%/NTX-Co-7%). NTX-Co transdermal flux (n=7) was measured through heat-separated human cadaver skin using Franz Cell Diffusion cells at 32° C. As shown in FIG. 16, the data show that 4:3 naltrexone: 5-methyl-2-furaldehyde cocrystal particles flux is lower in the absence of lidocaine.

The claimed invention is:

1. 4:3 naltrexone: 5-methyl-2-furaldehyde cocrystal.

2. 4:3 naltrexone: 5-methyl-2-furaldehyde cocrystal characterized by one or more of:
   (a) a powder x-ray diffraction pattern as in FIG. 1 having at least peaks selected from 11.5, 13.1, and 17.5°2θ±0.2 ° 2θ;
   (b) an infra-red spectrum as in FIG. 4;
   (c) a $P2_12_12_1$ space group at a temperature of 120K; or
   (d) unit cell dimensions of a=12.5936 (5) Å, b=13.9816 (6) Å, c=47.6259 (18) Å, α=90°, β=90°, and γ=90° at a temperature of 120K.

3. A drug-in-adhesive transdermal patch comprising:
   a backing layer;
   an adhesive layer disposed on the backing layer, the adhesive layer comprising a pressure sensitive adhesive, fentanyl or an analog thereof selected from the group consisting of fentanyl, sufentanil, alfentanil, and remifentanil, and a 4:3 naltrexone: 5-methyl-2-furaldehyde cocrystal according to claim 1; and
   a release layer disposed on the adhesive layer opposite the backing layer.

4. A drug-in-adhesive transdermal patch of claim 3, wherein the adhesive layer comprises 0.05 to about 1.75 mg/cm$^2$ of fentanyl or an analog thereof and an amount of 4:3 naltrexone: 5-methyl-2-furaldehyde cocrystal present having a molar ratio of naltrexone to fentanyl or an analog thereof ranging from about 0.075:1 to about 30:1.

5. A drug-in-adhesive transdermal patch of claim 4, wherein the pressure sensitive adhesive is a silicone pressure sensitive adhesive and the fentanyl or analog thereof is fentanyl.

6. A drug-in-adhesive transdermal patch of claim 4, wherein the fentanyl or analog thereof is fentanyl.

7. A method of treating pain comprising the step of applying a drug-in-adhesive transdermal patch according to claim 4 to the skin of a patient in need thereof.

8. A drug-in-adhesive transdermal patch comprising:
   a backing layer;
   an adhesive layer disposed on the backing layer, the adhesive layer comprising a pressure sensitive adhesive, an opioid agonist, and a 4:3 naltrexone: 5-methyl-2-furaldehyde cocrystal according to claim 1; and
   a release layer disposed on the adhesive layer opposite the backing layer.

9. An improved transdermal patch for administering fentanyl or an analog thereof selected from the group consisting of fentanyl, sufentanil, alfentanil, and remifentanil, or for administering a mu opioid agonist, wherein the improvement comprises the transdermal patch containing a 4:3 naltrexone: 5-methyl-2-furaldehyde cocrystal in an abuse limiting amount.

10. The improved transdermal patch of claim 9, wherein the transdermal patch is a drug-in-adhesive transdermal patch or a reservoir transdermal patch.

11. A method of treating pain comprising the step of applying a drug-in-adhesive transdermal patch according to claim 9 to the skin of a patient in need thereof to treat pain in a patient in need thereof.

12. A drug-in-adhesive transdermal patch comprising:
   a backing layer;
   an adhesive layer disposed on the backing layer, the adhesive layer comprising a pressure sensitive adhesive, fentanyl or an analog thereof selected from the group consisting of fentanyl, sufentanil, alfentanil, and remifentanil, and a 4:3 naltrexone: 5-methyl-2-furaldehyde cocrystal according to claim 2; and
   a release layer disposed on the adhesive layer opposite the backing layer.

13. A drug-in-adhesive transdermal patch of claim 12, wherein the adhesive layer comprises 0.05 to about 1.75 mg/cm$^2$ of fentanyl or an analog thereof and an amount of 4:3 naltrexone: 5-methyl-2-furaldehyde cocrystal present having a molar ratio of naltrexone to fentanyl or an analog thereof ranging from about 0.075:1 to about 30:1.

14. A drug-in-adhesive transdermal patch of claim 13, wherein the pressure sensitive adhesive is a silicone pressure sensitive adhesive and the fentanyl or analog thereof is fentanyl.

15. A drug-in-adhesive transdermal patch of claim 13, wherein the fentanyl or analog thereof is fentanyl.

16. A drug-in-adhesive transdermal patch comprising:
   a backing layer;

an adhesive layer disposed on the backing layer, the adhesive layer comprising a pressure sensitive adhesive, an opioid agonist, and a 4:3 naltrexone: 5-methyl-2-furaldehyde cocrystal according to claim 2; and a release layer disposed on the adhesive layer opposite the backing layer.

\* \* \* \* \*